(12) United States Patent
Hembrough et al.

(10) Patent No.: US 10,585,099 B2
(45) Date of Patent: Mar. 10, 2020

(54) SRM/MRM ASSAYS FOR CANCER

(71) Applicant: EXPRESSION PATHOLOGY, INC., Rockville, MD (US)

(72) Inventors: Todd Hembrough, Gaithersburg, MD (US); Fabiola Cecchi, Washington, DC (US); Sarit Schwartz, Rockville, MD (US); Kerry Scott, Germantown, MD (US)

(73) Assignee: EXPRESSION PATHOLOGY, INC., Rockville, MD (US)

( * ) Notice: Subject to any disclaimer, the term of this patent is extended or adjusted under 35 U.S.C. 154(b) by 72 days.

(21) Appl. No.: 15/811,049

(22) Filed: Nov. 13, 2017

(65) Prior Publication Data

US 2018/0188251 A1 Jul. 5, 2018

Related U.S. Application Data

(60) Provisional application No. 62/420,479, filed on Nov. 10, 2016.

(51) Int. Cl.

| | |
|---|---|
| *G01N 33/53* | (2006.01) |
| *G01N 33/567* | (2006.01) |
| *A01N 1/00* | (2006.01) |
| *G01N 33/574* | (2006.01) |
| *G01N 33/68* | (2006.01) |
| *C07K 14/705* | (2006.01) |
| *G01N 30/02* | (2006.01) |
| *C12Q 1/37* | (2006.01) |
| *H01J 49/26* | (2006.01) |

(52) U.S. Cl.
CPC ..... *G01N 33/574* (2013.01); *C07K 14/70517* (2013.01); *C07K 14/70578* (2013.01); *C07K 14/70596* (2013.01); *C12Q 1/37* (2013.01); *G01N 30/02* (2013.01); *G01N 33/57484* (2013.01); *G01N 33/68* (2013.01); *G01N 33/6848* (2013.01); *G01N 33/6851* (2013.01); *H01J 49/26* (2013.01); *G01N 2030/027* (2013.01); *G01N 2333/70503* (2013.01)

(58) Field of Classification Search
None
See application file for complete search history.

(56) References Cited

U.S. PATENT DOCUMENTS

2013/0288233 A1 10/2013 Murray
2014/0005282 A1* 1/2014 Krizman ............ G01N 33/4833
514/789
2017/0319722 A1* 11/2017 Agnew ................. A61K 51/08

FOREIGN PATENT DOCUMENTS

WO 2016004233 A2 1/2016

OTHER PUBLICATIONS

Hembrough et al, 2013. J Mol. Diag. 15:454-465 (Year: 2013).*
Lafarge et al. 2015. Leukemia Res. 39:773-778 (Year: 2015).*
Nilsson et al. 2005. Exper. Hemat. 33:1500-1507 (Year: 2005).*
Ranheim et al. 1995. Blood. 85:3556-3565 (Year: 1995).*
International Search Report for PCT Application No. PCT/US2017/061036 dated Feb. 9, 2018.
Written Opinion for PCT Application No. PCT/US2017/061036 dated Feb. 9, 2018.
International Preliminary Report on Patentability from PCT Application No. PCT/US2017/061036 dated May 23, 2019.

* cited by examiner

*Primary Examiner* — Shulamith H Shafer
(74) *Attorney, Agent, or Firm* — Harness, Dickey and Pierce, P.L.C.

(57) ABSTRACT

Methods are provided for quantifying specific proteins directly in biological samples that have been fixed in formalin by SRM/MRM assay. Such biological samples are chemically preserved and fixed wherein said biological sample is selected from tissues and cells treated with formaldehyde containing agents/fixatives including formalin-fixed tissue/cells, formalin-fixed/paraffin embedded (FFPE) tissue/cells, FFPE tissue blocks and cells from those blocks. A protein digest is prepared from the biological sample using, for example, the Liquid Tissue reagents and protocol and a designated protein is quantitated in the digest sample by the method of SRM/MRM mass spectrometry by quantitating in the protein sample at least one or more of the described peptides. The proteins that can be detected and/or quantitated are CD3D, B7H3, B7-2, STAT1, GBP1, GPNMB, CD27, CD3E, and CD8.

9 Claims, No Drawings

Specification includes a Sequence Listing.

SEQUENCE LISTING

```
<160> NUMBER OF SEQ ID NOS: 15

<210> SEQ ID NO 1
<211> LENGTH: 9
<212> TYPE: PRT
<213> ORGANISM: Homo sapiens

<400> SEQUENCE: 1

Ile Pro Ile Glu Glu Leu Glu Asp Arg
1               5

<210> SEQ ID NO 2
<211> LENGTH: 12
<212> TYPE: PRT
<213> ORGANISM: Homo sapiens

<400> SEQUENCE: 2

Leu Ser Gly Ala Ala Asp Thr Gln Ala Leu Leu Arg
1               5                   10

<210> SEQ ID NO 3
<211> LENGTH: 10
<212> TYPE: PRT
<213> ORGANISM: Homo sapiens

<400> SEQUENCE: 3

Gln Leu Val His Ser Phe Thr Glu Gly Arg
1               5                   10
```

```
<210> SEQ ID NO 4
<211> LENGTH: 18
<212> TYPE: PRT
<213> ORGANISM: Homo sapiens

<400> SEQUENCE: 4

Asn Pro Val Leu Gln Gln Asp Ala His Ser Ser Val Thr Ile Thr Pro
1               5                   10                  15

Gln Arg

<210> SEQ ID NO 5
<211> LENGTH: 10
<212> TYPE: PRT
<213> ORGANISM: Homo sapiens

<400> SEQUENCE: 5

Gly Leu Tyr Asp Val Val Ser Val Leu Arg
1               5                   10

<210> SEQ ID NO 6
<211> LENGTH: 11
<212> TYPE: PRT
<213> ORGANISM: Homo sapiens

<400> SEQUENCE: 6

Ile Thr Glu Asn Pro Val Ser Thr Gly Glu Lys
1               5                   10

<210> SEQ ID NO 7
<211> LENGTH: 12
<212> TYPE: PRT
<213> ORGANISM: Homo sapiens

<400> SEQUENCE: 7

Glu Leu Ser Ala Val Thr Phe Pro Asp Ile Ile Arg
1               5                   10

<210> SEQ ID NO 8
<211> LENGTH: 9
<212> TYPE: PRT
<213> ORGANISM: Homo sapiens

<400> SEQUENCE: 8

Leu Gln Glu Leu Asn Tyr Asn Leu Lys
1               5

<210> SEQ ID NO 9
<211> LENGTH: 8
<212> TYPE: PRT
<213> ORGANISM: Homo sapiens

<400> SEQUENCE: 9

Glu Ala Ile Glu Val Phe Ile Arg
1               5

<210> SEQ ID NO 10
<211> LENGTH: 9
<212> TYPE: PRT
<213> ORGANISM: Homo sapiens

<400> SEQUENCE: 10

Asn Glu Ile Gln Asp Leu Gln Thr Lys
1               5
```

```
<210> SEQ ID NO 11
<211> LENGTH: 9
<212> TYPE: PRT
<213> ORGANISM: Homo sapiens

<400> SEQUENCE: 11

Ala Tyr Val Pro Ile Ala Gln Val Lys
1               5

<210> SEQ ID NO 12
<211> LENGTH: 14
<212> TYPE: PRT
<213> ORGANISM: Homo sapiens

<400> SEQUENCE: 12

Glu Glu Glu Gly Ser Thr Ile Pro Ile Gln Glu Asp Tyr Arg
1               5                   10

<210> SEQ ID NO 13
<211> LENGTH: 10
<212> TYPE: PRT
<213> ORGANISM: Homo sapiens

<400> SEQUENCE: 13

Thr Leu Ser Thr His Trp Pro Pro Gln Arg
1               5                   10

<210> SEQ ID NO 14
<211> LENGTH: 9
<212> TYPE: PRT
<213> ORGANISM: Homo sapiens

<400> SEQUENCE: 14

Asp Leu Tyr Ser Gly Leu Asn Gln Arg
1               5

<210> SEQ ID NO 15
<211> LENGTH: 11
<212> TYPE: PRT
<213> ORGANISM: Homo sapiens

<400> SEQUENCE: 15

Thr Trp Asn Leu Gly Glu Thr Val Glu Leu Lys
1               5                   10
```

SRM/MRM ASSAYS FOR CANCER

This application claims priority to U.S. Provisional Application Ser. No. 62/420,479, filed Nov. 10, 2016, entitled SRM/MRM Assays for Cancer, the contents of which are hereby incorporated by reference in their entirety. This application also contains a sequence listing submitted electronically via EFS-web, which serves as both the paper copy and the computer readable form (CRF) and consists of a file entitled "SequenceListing_3900_0039C", which was created on Nov. 8, 2017 which is 2,630 bytes in size, and which is also incorporated by reference in its entirety.

INTRODUCTION

The level of protein expression in patient tumor tissue of one or more of the proteins CD3D, B7H3, B7-2, STAT1, GBP1, GPNMB, CD27, CD3E, and/or CD8 is determined by quantitating a specified peptide derived from subsequences of each of the full-length proteins. Each peptide is detected using mass spectrometry-based Selected Reaction Monitoring (SRM), also referred to as Multiple Reaction Monitoring (MRM), and which is referred to herein as an SRM/MRM assay. An SRM/MRM assay is used to detect the presence and quantitatively measure the amount of a specified fragment peptide directly in cells procured from cancer patient tissue, such as, for example formalin fixed cancer tissue.

The quantitation is relative or absolute. When absolute quantitation is required the measured level of each peptide is compared to a known amount of a labeled reference peptide having the same amino acid sequence as the measured peptide. The peptides are unique to a specific protein and therefore one peptide molecule is derived from one protein molecule and this allows quantitation of the intact protein from which the peptide is derived. The measurements of protein expression can be used for diagnosis of cancer, staging of the cancer, prognosis of cancer progression, predicting the likelihood of clinical response to various cancer treatments and therapies, and the like.

DETAILED DESCRIPTION

Measured Proteins

CD3D (T-cell surface glycoprotein CD3 delta chain) is a transmembrane signaling protein that is also a regulator of gene transcription. CD3D is involved in the cell receptor signaling pathway that functions in the process of T cell differentiation. CD3D appears to be an important protein in the regulation of the cancer immune response and is therefore a potential target that can be modulated by small molecules or biological agents to enhance an immune-based cancer therapy.

B7H3 (CD276) is an immune checkpoint molecule that is an essential regulator of the immunological synapse which enables the fine-tuning of the immune response. B7H3 is expressed by some solid tumors in order to subvert and evade immunosurveillance, and is the target of multiple anticancer therapeutic agents currently in development by the pharmaceutical companies.

B7-2 (CD86) is a type I membrane protein that is a member of the immunoglobulin superfamily. B7-2 is primarily expressed on antigen-presenting cells to provide costimulatory signals necessary for T cell activation and survival. It is the ligand for two different proteins on the T cell surface: CD28 (for autoregulation and intercellular association) and CTLA4 (for attenuation of regulation and cellular disassociation). B7-2 works in tandem with CD80 to prime T-cells and is instrumental in tightly regulating the T-cell cancer immune response. Understanding the expression pattern of B7-2 in a cancer patient can better inform an immune-based treatment approach to cancer therapy.

STAT1 (Signal transducer and activator of transcription 1) is a transcription factor involved in upregulating genes due to a signal by either type I, type II, or type III interferons. In response to IFN-γ stimulation, STAT1 forms homodimers or heterodimers with STAT3 that bind to the GAS (Interferon-Gamma-Activated Sequence) promoter element; in response to either IFN-α or IFN-β stimulation, STAT1 forms a heterodimer with STAT2 that can bind the ISRE (Interferon-Stimulated Response Element) promoter element. Thus binding of the promoter element leads to an increased expression of Interferon-Stimulated Genes (ISGs) STAT1 is a member of the signal transducer and activator of transcription (STAT) protein family that Mediate many aspects of cellular immunity, proliferation, apoptosis and differentiation. Dysregulation of this pathway is frequently observed in primary tumors and leads to increased angiogenesis, enhanced survival of tumors and immunosuppression. Understanding the protein expression status of STAT1 in a cancer patient can better inform an immune-based treatment approach to cancer therapy.

GBP1 (Interferon-induced guanylate-binding protein 1) is a protein that belongs to the dynamin superfamily of large GTPases. Guanylate binding protein expression is induced by interferon and thus is an important part of the cancer immune response. Guanylate binding proteins are characterized by their ability to specifically bind guanine nucleotides (GMP, GDP, and GTP) and are distinguished from the GTP-binding proteins by the presence of 2 binding motifs rather than 3. GBP1 plays an important role in the IFN-γ-dependent, cell-autonomous control of viral infection control and likely plays a broader role in the mechanism of the cancer immune response. Further elucidation of the function of this protein in the cancer immune response will likely inform cancer immunotherapy treatment decisions.

GPNMB (Transmembrane glycoprotein NMB) is a type I transmembrane glycoprotein which shows homology to the pmel17 precursor, a melanocyte-specific protein. GPNMB has been reported to be expressed in various cell types including melanocytes, osteoclasts, osteoblasts, dendritic cells, and it is overexpressed in various cancer cell types. GPNMB was originally identified as expressed in poorly metastatic human melanoma cell lines and xenografts and not expressed in highly metastatic cell lines. Several studies have identified high GPNMB expression in aggressive melanoma, glioma, and breast cancer specimens. GPNMB is the target of the antibody glembatumumab which is used in the antibody-drug conjugate glembatumumab-vedotin. This targeted cancer therapy is currently in clinical trials for melanoma and breast cancer.

CD27 is a member of the tumor necrosis factor receptor superfamily and is a costimulatory immune checkpoint molecule. CD27 is required for generation and long-term maintenance off cell immunity. It binds to ligand CD70, and plays a key role in regulating B-cell activation and immunoglobulin synthesis. CD27-binding protein (SIVA), a proapoptotic protein, can bind to this receptor and is thought to play an important role in the apoptosis induced by this receptor. Varlilumab is an antibody that binds to CD27 and is one candidate cancer therapy agent currently used as an experimental immune-based cancer treatment.

CD3E (CD3-epsilon polypeptide) is a protein that together with CD3-gamma, -delta and -zeta, and the T-cell receptor alpha/beta and gamma/delta heterodimers, forms the T cell receptor-CD3 complex. This complex plays an important role in coupling antigen recognition to several intracellular signal-transduction pathways. The epsilon polypeptide plays an essential role in T-cell development and understanding the expression status of this protein can inform an immune-based cancer treatment approach.

CD8 (duster of differentiation 8) is a transmembrane glycoprotein that serves as a co-receptor for the T cell receptor (TCR). The CD8 co-receptor is predominantly expressed on the surface of cytotoxic T cells, but can also be found on natural killer cells, cortical thymocytes, and dendritic cells. It is expressed in T cell lymphoblastic lymphoma and hypo-pigmented mycosis fungoides. Like the TCR, CD8 binds to a major histocompatibility complex (MHC) molecule, but is specific for the class I MHC protein. Thus CD8 is a critical component of the cancer antigen presentation complex. Understanding the expression status of the CD8 protein can inform the immune-based cancer treatment decision.

The methods below provide quantitative proteomics-based assays that quantify each of the measured proteins in formalin fixed tissues from cancer patients. Data from the assays can be used to provide improved methods of treatment for cancer therapy, for example.

The SRM/MRM assays can be used to measure relative or absolute quantitative levels of the specific peptides from each of the measured proteins and therefore provide a means of measuring by mass spectrometry the amount of each of the proteins in a given protein preparation obtained from a biological sample. More specifically, the SRM/MRM assay can measure these peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by references in their entirety. The methods described in U.S. Pat. No. 7,473,532 may conveniently be carried out using Liquid Tissue reagents and the protocol available from Expression Pathology Inc. (Rockville, Md.).

The most widely and advantageously available form of tissue from cancer patients is formalin fixed, paraffin embedded tissue. Formaldehyde/formalin fixation of surgically removed tissue is by far the most common method of preserving cancer tissue samples worldwide and is the accepted convention for standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of each of the specified proteins within the specific tissue samples (e.g., cancer tissue sample) of the patient or subject from whom the tissue (biological sample) was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond.

The assays described herein measures relative or absolute levels of specific unmodified peptides from the specified proteins and also can measure absolute or relative levels of specific modified peptides from each of the specified proteins. Examples of modifications include phosphorylated amino acid residues and glycosylated amino acid residues that are present on the peptides.

Relative quantitative levels of each of the proteins are determined by the SRM/MRM methodology, for example by comparing SRM/MRM signature peak areas (e.g., signature peak area or integrated fragment ion intensity) of an individual fragment peptide derived from a protein in different samples. Alternatively, it is possible to compare multiple SRM/MRM signature peak areas for multiple signature peptides, where each peptide has its own specific SRM/MRM signature peak, to determine the relative protein content in one biological sample with the content of the same protein(s) in one or more additional or different biological samples. In this way, the amount of a particular peptide, or peptides, from the subject protein(s), and therefore the amount of the designated protein(s), is determined relative to the same peptide, or peptides, across 2 or more biological samples under the same experimental conditions. In addition, relative quantitation can be determined for a given peptide, or peptides, from a given protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from a designated protein, and therefore the amount of that protein, is determined relative one to another within the same sample. These approaches generate quantitation of an individual peptide, or peptides, from a designated protein to the amount of another peptide, or peptides, between samples and within samples wherein the amounts as determined by signature peak area are relative one to another, regardless of the absolute weight to volume or weight to weight amounts of the selected peptide in the protein preparation from the biological sample. Relative quantitative data about individual signature peak areas between different samples are normalized to the amount of protein analyzed per sample. Relative quantitation can be performed across many peptides from multiple proteins and one or more of the designated proteins simultaneously in a single sample and/or across many samples to gain insight into relative protein amounts, such as one peptide/protein with respect to other peptides/proteins.

Absolute quantitative levels of the designated protein are determined by, for example, the SRM/MRM methodology whereby the SRM/MRM signature peak area of an individual peptide from the designated protein in a biological sample is compared to the SRM/MRM signature peak area of a spiked internal standard. In one embodiment, the internal standard is a synthetic version of the peptide derived from the designated protein that has the identical amino acid sequence but contains one or more amino acid residues labeled with one or more heavy isotopes. Such isotope labeled internal standards are synthesized so that, when analyzed by mass spectrometry, a standard generates a predictable and consistent SRM/MRM signature peak that is different and distinct from the native peptide signature peak and which can be used as a comparator peak. Thus when the internal standard is spiked into a protein preparation from a biological sample in known amounts and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to improve methods of treating cancer by determining in advance which therapeutic agent would be most advantageous for use in treating a patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer.

Assays of protein levels from one, some, or all of the designated proteins can also be used to diagnose the stage of cancer in a patient or subject diagnosed with cancer by, for example, comparing the protein levels to those observed in normal tissue. The level of an individual peptide derived from a designated protein is defined as the molar amount of the peptide determined by the SRM/MRM assay per total amount of protein lysate analyzed. Information regarding a designated protein or proteins can thus be used to aid in determining the stage or grade of a cancer by correlating the level of the protein(s) (or fragment peptides from the proteins) with levels observed in normal tissues.

Once the quantitative amount of one or more of the designated proteins has been determined in the cancer cells, that information can be matched to a list of therapeutic agents (chemical and biological) developed to specifically treat cancer tissue that is characterized by, for example, abnormal expression of the assayed protein or protein(s). The matching of information from a protein assay to a list of therapeutic agents that specifically targets, for example, the designated protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions.

In principle, any predicted peptide derived from a designated protein, prepared for example by digesting with a protease of known specificity (e.g. trypsin), can be used as a surrogate reporter to determine the abundance of a designated protein in a sample using a mass spectrometry-based SRM/MRM assay. Similarly, any predicted peptide sequence containing an amino acid residue at a site that is known to be potentially modified in the designated protein also might potentially be used to assay the extent of modification of the designated protein in a sample. Surprisingly, however, it has been found that it is impossible to predict a priori which, if any, peptide can be reliably and reproducibly detected and quantitated in protein digests prepared from formalin-fixed tissue. Moreover, it has been found that results obtained in fresh and frozen tissue are not predictive of results in formalin-fixed tissue.

Suitable fragment peptides derived from a designated protein may be generated by a variety of means including by the use of the Liquid Tissue protocol provided in U.S. Pat. No. 7,473,532. The Liquid Tissue protocol and reagents are capable of producing peptide samples suitable for mass spectroscopic analysis from formalin fixed paraffin embedded tissue by proteolytic digestion of the proteins III the tissue/biological sample. In the Liquid Tissue protocol the tissue/biological is heated in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris based buffer, or a buffer containing a detergent). Following heat treatment the tissue/biological sample is treated with one or more proteases, including but not limited to trypsin, chymotrypsin, pepsin, and endoproteinase Lys-C for a time sufficient to disrupt the tissue and cellular structure of said biological sample. The result of the heating and proteolysis is a liquid, soluble, dilutable biomolecule lysate.

Surprisingly, it was found that many potential peptide sequences from the proteins listed above are unsuitable or ineffective for use in mass spectrometry-based SRM/MRM assays for reasons that are not immediately evident. As it was not possible to predict the most suitable peptides for MRM/SRM assay, it was necessary to experimentally identify modified and unmodified peptides in actual Liquid Tissue lysates to develop a reliable and accurate SRM/MRM assay for each designated protein. While not wishing to be bound by any theory, it is believed that some peptides might, for example, be difficult to detect by mass spectrometry because they do not ionize well or produce fragments distinct from other proteins. Peptides may also fail to resolve well in separation (e.g., liquid chromatography), or may adhere to glass or plastic ware.

The peptides found in Table I were derived from the respective designated proteins by protease digestion of all the proteins within a complex Liquid Tissue lysate prepared from cells procured from formalin fixed cancer tissue. Unless noted otherwise, in each instance the protease was trypsin. The Liquid Tissue lysate was then analyzed by mass spectrometry to determine those peptides derived from a designated protein that are detected and analyzed by mass spectrometry. Identification of a specific preferred subset of peptides for mass spectrometric analysis is based on; 1) experimental determination of which peptide or peptides from a protein ionize in mass spectrometry analyses of Liquid Tissue lysates, and 2) the ability of the peptide to survive the protocol and experimental conditions used in preparing a Liquid Tissue lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue reagents and protocol that entails collecting cells into a sample tube via tissue microdissection followed by heating the cells in the Liquid Tissue buffer for an extended period of time. Once the formalin-induced cross linking has been negatively affected, the tissue/cells are then digested to completion in a predictable manner using a protease, as for example including but not limited to the protease trypsin. Each protein lysate is reduced to a collection of peptides by digestion of intact polypeptides with the protease. Each Liquid Tissue lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is typically employed. Ion trap mass spectrometers however may be the best type of mass spectrometer for conducting global profiling of peptides.

Although an SRM/MRM assay can be developed and performed on any type of mass spectrometer, including a MALDI, ion trap, or triple quadrupole, the most advantageous instrument platform for an SRM/MRM assay is often considered to be a triple quadrupole instrument platform. Once as many peptides as possible were identified in a single MS analysis of a single lysate under the conditions employed, then that list of peptides was collated and used to determine the proteins that were detected in that lysate. That process was repeated for multiple Liquid Tissue lysates, and the very large list of peptides was collated into a single dataset. That type of dataset can be considered to represent the peptides that can be detected in the type of biological sample that was analyzed (after protease digestion), and specifically in a Liquid Tissue lysate of the biological sample, and thus includes the peptides for each of the designated proteins.

In one embodiment, the tryptic peptides identified as useful in the determination of absolute or relative amounts of the designated proteins are listed in Table 1. Each of these peptides was detected and quantitated by mass spectrometry in Liquid Tissue lysates prepared from formalin fixed, paraffin embedded tissue. Thus, each peptide can be used to develop a quantitative SRM/MRM assay for a designated protein in human biological samples, including directly in formalin fixed patient tissue.

TABLE 1

| SEQ ID NO | Protein | Peptide Sequence |
|---|---|---|
| SEQ ID NO 1 | CD3D | IPIEELEDR |
| SEQ ID NO 2 | CD3D | LSGAADTQALLR |
| SEQ ID NO 3 | B7H3 | QLVHSFTEGR |
| SEQ ID NO 4 | B7H3 | NPVLQQDAHSSVTITPQR |
| SEQ ID NO 5 | B7-2 | LHNLQIK |
| SEQ ID NO 6 | B7-2 | TSFDSDSWTLR |
| SEQ ID NO 7 | STAT1 | ELSAVTFPDIIR |
| SEQ ID NO 8 | STAT1 | LQELNYNLK |
| SEQ ID NO 9 | GBP1 | EAIEVFIR |
| SEQ ID NO 10 | GBP1 | NEIQDLQTK |
| SEQ ID NO 11 | GPNMB | AYVPIAQVK |
| SEQ ID NO 12 | CD27 | EEEGSTIPIQEDYR |
| SEQ ID NO 13 | CD27 | TLSTHWPPQR |
| SEQ ID NO 14 | CD3E | DLYSGLNQR |
| SEQ ID NO 15 | CD8 | TWNLGETVELK |

The tryptic peptides listed in Table 1 typically were detected from multiple Liquid Tissue lysates of multiple different formalin fixed tissues of different human organs including, for example, prostate, colon, and breast.

One consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, the most advantageous instrument platform for an SRM/MRM assay is often considered to be a triple quadrupole instrument platform. That type of a mass spectrometer presently is considered to be the most suitable instrument for analyzing a single isolated target peptide within a very complex protein lysate that may consist of hundreds of thousands to millions of individual peptides from all the proteins contained within a cell. The described method was used to: 1) identify candidate peptides from each designated protein that can be used for a mass spectrometry-based SRM/MRM assay for the designated protein, 2) develop an individual SRM/MRM assay, or assays, for target peptides from the designated protein in order to correlate and 3) apply quantitative assays to cancer diagnosis and/or choice of optimal therapy.

Assay Method

1. Identification of SRM/MRM candidate fragment peptides for a protein.
   a. Prepare a Liquid Tissue protein lysate from a formalin fixed biological sample using a protease or proteases, (that may or may not include trypsin), to digest proteins
   b. Analyze all protein fragments in the Liquid Tissue lysate on an ion trap tandem mass spectrometer and identify all fragment peptides from a designated protein, where individual fragment peptides do not contain any peptide modifications such as phosphorylations or glycosylations
   c. Analyze all protein fragments in the Liquid Tissue lysate on an ion trap tandem mass spectrometer and identify all fragment peptides from the protein that carry peptide modifications such as for example phosphorylated or glycosylated residues
   d. All peptides generated by a specific digestion method from an entire, full length protein can potentially be measured, but preferred peptides used for development of the SRM/MRM assay are those that are identified by mass spectrometry directly in a complex Liquid Tissue protein lysate prepared from a formalin fixed biological sample 2. Mass Spectrometry Assay for Fragment Peptides from a Designated Protein
   a. SRM/MRM assay on a triple quadrupole mass spectrometer for individual fragment peptides identified in a Liquid Tissue lysate is applied to peptides from the protein
      i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
      ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
      iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer.
   b. Perform SRM/MRM analysis so that the amount of the fragment peptide of the protein that is detected, as a function of the unique SRM/MRM signature peak area from an SRM/MRM mass spectrometry analysis, can indicate both the relative and absolute amount of the protein in a particular protein lysate.
      i. Relative quantitation may be achieved by:
         1. Determining increased or decreased presence of the protein by comparing the SRM/MRM signature peak area from a given fragment peptide detected in a Liquid Tissue lysate from one formalin fixed biological sample to the same SRM/MRM signature peak area of the same fragment peptide in at least a second, third, fourth or more Liquid Tissue lysates from least a second, third, fourth or more formalin fixed biological samples.
         2. Determining increased or decreased presence of the protein by comparing the SRM/MRM signature peak area from a given fragment peptide detected in a Liquid Tissue lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
         3. Determining increased or decreased presence of the protein by comparing the SRM/MRM signature peak area for a given fragment peptide to the SRM/MRM signature peak areas from other fragment peptides derived from different proteins within the same Liquid Tissue lysate from the formalin fixed biological sample in order to normalize changing levels of a protein to levels of other proteins that do not change their levels of expression under various cellular conditions.
         4. These assays can be applied to both unmodified fragment peptides and for modified fragment peptides of the protein, where the modifications include but are not limited to phosphorylation and/or glycosylation, and where the relative levels of modified peptides are determined in the same manner as determining relative amounts of unmodified peptides.
      i. Absolute quantitation of a given peptide may be achieved by comparing the SRM/MRM signature peak area for a given fragment peptide from the designated protein in an individual biological sample to the SRM/MRM signature peak area of an internal fragment peptide standard spiked into the protein lysate from the biological sample
         1. The internal standard is a labeled synthetic version of the fragment peptide from the designated protein that is being interrogated. This standard is spiked into a sample in known amounts, and the SRM/MRM signature peak area can be determined for both the internal fragment peptide standard and the native fragment peptide in the biological sample separately, followed by comparison of both peak areas.
         2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
         3. Apply Fragment Peptide Quantitation to Cancer Diagnosis and Treatment
            a. Perform relative and/or absolute quantitation of fragment peptide levels of the designated protein and demonstrate that the previously-determined association, as well understood in the field of cancer, of expression of the designated protein to the stage/grade/status of cancer in patient tumor tissue is confirmed.
            b. Perform relative and/or absolute quantitation of fragment peptide levels of the designated protein and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy Specific and unique characteristics about specific fragment peptides from each designated protein were developed by analysis of all fragment peptides on both an ion trap and triple quadrupole mass spectrometers. That information must be determined experimentally for each and every candidate SRM/MRM peptide directly in Liquid Tissue lysates from formalin fixed samples/tissue; because, interestingly, not all peptides from any designated protein can be detected in such lysates using SRM/MRM as described herein, indicating that fragment peptides not detected cannot be considered candidate peptides for developing an SRM/MRM assay for use in quantitating peptides/proteins directly in Liquid Tissue lysates from formalin fixed samples/tissue.

A particular SRM/MRM assay for a specific fragment peptide is performed on a triple quadrupole mass spectrometer. An experimental sample analyzed by a particular protein SRM/MRM assay is, for example, a Liquid Tissue protein lysate prepared from a tissue that had been formalin fixed and paraffin embedded. Data from such as assay indicates the presence of the unique SRM/MRM signature peak for this fragment peptide in the formalin fixed sample.

Specific transition ion characteristics for this peptide are used to quantitatively measure a particular fragment peptide in formalin fixed biological samples. These data indicate absolute amounts of this fragment peptide as a function of the molar amount of the peptide per microgram of protein lysate analyzed. Assessment of corresponding protein levels in tissues based on analysis of formalin fixed patient-derived tissue can provide diagnostic, prognostic, and therapeutically-relevant information about each particular patient. In one embodiment, this disclosure describes a method for measuring the level of each of the proteins listed in Table 1 in a biological sample, comprising detecting and/or quantifying the amount of one or more modified or unmodified fragment peptides in a protein digest prepared from said biological sample using mass spectrometry; and calculating the level of modified or unmodified protein in said sample; and wherein said level is a relative level or an absolute level. In a related embodiment, quantifying one or more fragment peptides comprises determining the amount of the each of the fragment peptides in a biological sample by comparison to an added internal standard peptide of known amount, wherein each of the fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of a designated protein a biological sample described herein (or fragment peptides as surrogates thereof) may be used as a diagnostic indicator of cancer in a patient or subject. In one embodiment, the results from measurements of the level of a designated protein may be employed to determine the diagnostic stage/grade/status of a cancer by correlating (e.g., comparing) the level of the protein found in a tissue with the level of that protein found in normal and/or cancerous or precancerous tissues.

Because both nucleic acids and protein can be analyzed from the same Liquid Tissue biomolecular preparation it is possible to generate additional information about disease diagnosis and drug treatment decisions from the nucleic acids in same sample upon which proteins were analyzed. For example, if a designated protein is expressed by certain cells at increased levels, when assayed by SRM the data can provide information about the state of the cells and their potential for uncontrolled growth, potential drug resistance and the development of cancers can be obtained. At the same time, information about the status of the corresponding genes and/or the nucleic acids and proteins they encode (e.g., mRNA molecules and their expression levels or splice variations) can be obtained from nucleic acids present in the same Liquid Tissue biomolecular preparation can be assessed simultaneously to the SRM analysis of the designated protein. Any gene and/or nucleic acid not from the designated protein and which is present in the same biomolecular preparation can be assessed simultaneously to the SRM analysis of the designated protein. In one embodiment, information about the designated protein and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

The invention claimed is:

1. A method for measuring the level of a protein in a biological sample of formalin fixed tissue, the method comprising;
    detecting and quantifying by mass spectrometry an amount of one or more of CD3D, B7H3, B7-2, STAT1, GBP1, GPNMB, CD27, CD3E, and CD8 fragment peptides in a protein digest prepared from said biological sample; and
    calculating the level of said protein in said biological sample;
    wherein the protein digest comprises a trypsin digest, and wherein the one or more of CD3D, B7H3, B7-2, STAT1, GBP1, GPNMB, CD27, CD3E, and CD8 fragment peptides comprises an amino acid sequence as set forth in SEQ ID NOs:1-15.

2. The method of claim 1, further comprising the step of fractionating said protein digest prior to detecting and quantifying the amount of the one or more fragment peptides.

3. The method of claim 2, wherein said fractionating step is selected from the group consisting of liquid chromatography, nanoreversed phase liquid chromatography, high performance liquid chromatography, and reverse phase high performance liquid chromatography.

4. The method of claim 1, wherein the tissue is paraffin embedded tissue.

5. The method of claim 1, wherein the tissue is obtained from a tumor.

6. The method of claim 1, wherein quantifying said fragment peptide comprises comparing an amount of said fragment peptide in one biological sample to an amount of the same fragment peptide in a different and separate biological sample.

7. The method of claim 1, wherein quantifying said fragment peptide comprises determining the amount of said fragment peptide in the biological sample by comparison to an added internal standard peptide of known amount having the same amino acid sequence.

8. The method of claim 7, wherein the internal standard peptide is an isotopically labelled peptide.

9. The method of claim 8, wherein the isotopically labelled internal standard peptide comprises one or more heavy stable isotopes selected from $^{18}O$, $^{17}O$, $^{34}S$, $^{15}N$, $^{13}C$, and $^{2}H$ and a combination thereof.

* * * * *